(12) United States Patent
Fan et al.

(10) Patent No.: US 9,108,190 B1
(45) Date of Patent: Aug. 18, 2015

(54) RAPID SYNTHESIS OF BETA ZEOLITES

(71) Applicants: Wei Fan, Amherst, MA (US);
Chun-Chih Chang, Amherst, MA (US);
Paul Dornath, Amherst, MA (US);
Zhuopeng Wang, Amherst, MA (US)

(72) Inventors: Wei Fan, Amherst, MA (US);
Chun-Chih Chang, Amherst, MA (US);
Paul Dornath, Amherst, MA (US);
Zhuopeng Wang, Amherst, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/025,557

(22) Filed: Sep. 12, 2013

Related U.S. Application Data

(60) Provisional application No. 61/700,066, filed on Sep. 12, 2012.

(51) Int. Cl.
| | |
|---|---|
| *B01J 29/89* | (2006.01) |
| *B01J 29/04* | (2006.01) |
| *C07D 307/50* | (2006.01) |
| *B01J 29/76* | (2006.01) |
| *C01B 39/06* | (2006.01) |
| *C01B 39/08* | (2006.01) |
| *B01J 29/88* | (2006.01) |
| *C07H 1/00* | (2006.01) |
| *B01J 29/70* | (2006.01) |

(52) U.S. Cl.
CPC *B01J 29/89* (2013.01); *B01J 29/04* (2013.01); *B01J 29/7007* (2013.01); *B01J 29/7057* (2013.01); *B01J 29/7615* (2013.01); *B01J 29/88* (2013.01); *C01B 39/06* (2013.01); *C01B 39/065* (2013.01); *C01B 39/087* (2013.01); *C07D 307/50* (2013.01); *C07H 1/00* (2013.01)

(58) Field of Classification Search
CPC .... C01B 39/06; C01B 39/065; C01B 39/087; B01J 29/04; B01J 29/88; B01J 29/89; B01J 29/7007; B01J 29/7057; B01J 29/7615
See application file for complete search history.

(56) References Cited

U.S. PATENT DOCUMENTS

| | | | | |
|---|---|---|---|---|
| 4,965,059 | A | * | 10/1990 | Vaughan ................. 423/707 |
| 5,271,761 | A | * | 12/1993 | Skeels et al. ............. 95/116 |
| 5,968,473 | A | | 10/1999 | Valencia et al. |
| 6,191,323 | B1 | | 2/2001 | Nemeth et al. |
| 7,922,995 | B2 | * | 4/2011 | Vermeiren et al. ........ 423/713 |
| 8,206,683 | B2 | * | 6/2012 | Wang et al. ............. 423/705 |
| 2005/0113604 | A1 | * | 5/2005 | Canos et al. ............. 562/421 |
| 2011/0207923 | A1 | | 8/2011 | Moliner-Marin et al. |
| 2012/0330065 | A1 | * | 12/2012 | Corma Canos et al. ..... 568/445 |
| 2013/0202524 | A1 | * | 8/2013 | Maurer et al. ............ 423/709 |

OTHER PUBLICATIONS

Corma, A. et al. Sn-zeolite beta as a heterogeneous chemoselective catalyst for Baeyer-Villiger oxidations. Nature 412 (2001): 423-425.

(Continued)

*Primary Examiner* — David M Brunsman
(74) *Attorney, Agent, or Firm* — Burns & Levinson LLP; Janine M. Susan

(57) ABSTRACT

The invention provides methods for rapidly synthesizing heteroatom containing zeolites including Sn-Beta, Si-Beta, Ti-Beta, Zr-Beta and Fe-Beta. The methods for synthesizing heteroatom zeolites include using well-crystalline zeolite crystals as seeds and using a fluoride-free, caustic medium in a seeded dry-gel conversion method. The Beta zeolite catalysts made by the methods of the invention catalyze both isomerization and dehydration reactions.

18 Claims, 15 Drawing Sheets

(56) References Cited

OTHER PUBLICATIONS

Corma, A. et al. Water-resistant solid Lewis acid catalysts: Meerwein-Ponndorf-Verley and Oppenauer reactions catalyzed by tin-beta zeolite. Journal of Catalysis 215 (2003): 294-304.

Lew, C.M. et al. Tin-containing zeolite for the isomerization of cellulosic sugars. Microporous Mesoporous Mater 153 (2012): 55-58.

Moliner, M. et al. Tin-containing zeolites are highly active catalysts for the isomerization of glucose in water. Proc. Natl. Acad. Sci. U.S.A. 107 (2010): 6164-6168.

* cited by examiner

A)

B)

A)

B)

C)

A)

B)

A)

B)

A)

B)

RAPID SYNTHESIS OF BETA ZEOLITES

CROSS-REFERENCE TO RELATED APPLICATIONS

This application claims priority to U.S. Provisional Application No. 61/700,066 filed Sep. 12, 2012 and entitled RAPID SYNTHESIS OF BETA ZEOLITES, the entire contents of which are incorporated herein by reference for all purposes.

STATEMENT REGARDING FEDERALLY SPONSORED RESEARCH OR DEVELOPMENT

This invention was made, in part, with United States Government support from the Catalysis Center for Energy Innovation, an Energy Frontier Research Center funded by the U.S. Department of Energy, Office of Science, Office of Basic Energy Sciences under Award Number DE-SC0001004. The United States Government has certain rights in the invention.

BACKGROUND OF THE INVENTION

Because of their unique catalytic activity and excellent hydrothermal stability, zeolites, aluminosilicate molecular sieves, have been extensively used in petrochemical processing and production of high-value chemicals and biofuels from naturally abundant biomass. Instead of being used as solid Brønsted acid catalysts, molecular sieves containing tetrahedrally coordinated Ti and Sn have been explored as solid Lewis acid catalysts for redox reactions. Ti-containing, high-silica molecular sieves with the zeolite beta topology (Ti-Beta) and MFI topology (TS-1) have been employed for various selective oxidation reactions, such as olefin epoxidation, selective oxidation of alcohols, hydroxylation of phenol and ammoximation of cyclohexanone. Sn-Beta, a tin-containing molecular sieve with the zeolite beta topology, has been used in the Meerwein-Ponndorf-Verley (MPV) reduction of aldehydes and ketones, the Meerwein-Ponndorf-Verley-Oppenauer (MPVO) oxidation of alcohols and the Baeyer-Villiger oxidation reaction. Recently, due to its particular Lewis acidic properties, Sn-Beta has been shown to catalyze the isomerization reactions of triose sugars (dihydroxyacetone and glyceraldehyde), pentose sugars (xylose and xylulose) and hexose sugars (glucose and fructose) with activities that are comparable to biological processes. In particular, it has been revealed that Sn-Beta is a water tolerant Lewis acid catalyst, and can catalyze the isomerization reactions in aqueous phase at low pH, which is most likely due to its hydrophobic nature derived from the high-silica microporous structure. Because of the unique properties, Sn-Beta has also been used for one-pot synthesis of 5-(hydroxymethyl)-furfural (HMF), an important precursor for the production of renewable polymers and biofuels, from glucose by combining with a homogeneous acid catalyst (HCl) in a biphasic system.

Although Sn-Beta has shown promising catalytic properties, its industrial applications and related researches in academia have been hindered by the difficulties in synthesizing this material, particularly the use of hydrofluoric acid and long crystallization time. In general, active Sn-Beta is synthesized using fluoride anion as a mineralizing agent under near-neutral conditions with a crystallization time of around 40 days. The long crystallization time could be due to the relatively low supersaturation degree and limited nucleation caused by fluoride anion and neutral pH used in the synthesis. To reduce the crystallization time, a seeded growth method was applied to the synthesis of Sn-Beta. However, it still requires from 22 days to 30 days to accomplish the synthesis.

BRIEF SUMMARY OF THE INVENTION

The invention described herein provides methods for rapidly synthesizing heteroatom containing zeolites including Sn-Beta, Si-Beta, Ti-Beta, Zr-Beta and Fe-Beta. The synthesis time is significantly reduced to 2 days with a yield of higher than 85%. In the methods of the invention (1) well-crystalline zeolite crystals (200 nm) were used as the seeds, and (2) to avoid the aggregation of the seeds, a stable suspension containing the well-crystalline zeolite seeds was prepared, and directly added into the synthesis mixture without calcination and drying. These two parameters enable the well-crystalline seeds to be uniformly distributed in the synthesis mixture enabling the significant reduction in the time needed for synthesizing Beta zeolites.

The invention described herein also provides methods for synthesizing Sn-Beta using (1) well-crystalline zeolite crystals (200 nm) as the seeds, and (2) avoiding the aggregation of the seeds by preparing a stable suspension containing the well-crystalline zeolite seeds and directly adding the stable suspension into the synthesis mixture without calcination and drying, and (3) where the synthesis temperature is 200° C. which reduces the crystallization time to 6 hours.

The invention described herein also provides methods for synthesizing Sn-Beta zeolite from fluoride-free, caustic medium by a seeded dry-gel conversion method.

The invention described herein also provides that the Beta zeolite catalysts made by the methods of the invention catalyze both the isomerization and dehydration reactions from which glucose and xylose are efficiently converted to 5-(hydroxymethyl)-furfural (HMF) and furfural, respectively.

According to various embodiments described herein, the present invention describes a method of synthesizing molecular sieves including the steps of: a) preparing a seed solution comprising aluminosilicate zeolite beta nanocrystals, b) dealuminating said nanocrystals, c) preparing a solution comprising a structure directing agent and a heteroatom source, d) adding the dealuminated nanocrystals to the solution of step c), e) allowing a gel to form, f) heating said gel at a temperature and a time sufficient to form a solid, g) filtering, washing and drying said solid, and h) calcining said solid.

According to various embodiments described herein, the gel is heated to at least 175° C. for 12 hours or less. In a preferred embodiment, the gel is heated to 200° C. for 6 hours.

According to various embodiments described herein, the aluminosilicate zeolite beta nanocrystals are well-crystalline 200 nm crystals having a crystallinity equal to or greater than 80% crystalline. The well-crystalline zeolite seeds are used to prepare a seed solution that is a stable suspension of well dispersed beta zeolite seeds.

According to various embodiments described herein, the dealuminating step involves directly treating the seed solution with a concentrated nitric acid solution. In a preferred embodiment, the method further involves collecting, washing and dispersing the dealuminated nanocrystals in liquid prior to step d).

According to various embodiments described herein, the structure directing agent can be a compound such as tetraethylammonium hydroxide solution (TEAOH), tetrabutylammonium hydroxide, tetramethylammonium hydroxide, 4,4'trimethylene bis(N-methyl N-benzyl-piperidinium) hydroxide, 1,2-diazabicyclo 2,2,2, octane, or dialkylbenzyl ammonium hydroxide.

According to various embodiments described herein, the heteroatom source can be a tin source, a titanium source, a silicon source, a zirconium source or an iron source. Tin sources include, but are not limited to, tin halides, tin oxides, tin alkoxides, tin(II) acetate and metallic tin. Examples of tin halides include tin tetrachloride and stannous dichloride. Examples of tin alkoxides include tin butoxide, tin ethoxide and tin propoxide. Silicon sources include, but are not limited to, amorphous silica, tetraalkylorthosilicate (e.g., tetraethylorthosilicate), colloidal silica, fumed silica and silica gels. Titanium sources include, but are not limited to, titanium halides and titanium alkoxides. Examples of titanium halides include titanium tetrachloride. Examples of titanium alkoxides include titanium ethoxide, titanium isopropoxide and titanium butoxide. Zirconium sources include, but are not limited to, zirconium oxyhalides, zirconium halides and zirconium alkoxides. A preferred zirconium source is zirconium oxychloride. Examples of zirconium alkoxides include zirconium propoxide, zirconium butoxide and zirconium ethoxide. Iron sources include, but are not limited to iron halides (e.g., iron chloride) and iron nitrate.

According to various embodiments described herein, the solution of step c) further comprises tetraethylorthosilicate (TEOS) and hydrofluoric acid (HF). In some preferred embodiments, the solution of step c) further comprises tetraethylorthosilicate (TEOS) and ammonium fluoride ($NH_4F$). In other preferred embodiments, the solution of step c) further comprises a caustic medium having a pH in the range of about 9 to about 13. The caustic medium can be sodium hydroxide (NaOH) or potassium hydroxide (KOH).

According to various embodiments described herein, the formed gel has a composition comprising $SiO_2$:0.5TEAOH: 0.5HF:$7H_2O$ or $SiO_2$:0.54TEAOH:0.54HF:0.008$SnO_2$: 7.5$H_2O$ or $SiO_2$:0.54TEAOH:0.54$NH_4$F:0.008$SnO_2$:7.5$H_2O$ or $SiO_2$:0.008$SnO_2$:0.22$TEA_2O$: 0.034 $Na_2O$.

According to various embodiments described herein, the solid obtained in step h) is a zeolite selected from the group consisting of Sn-Beta, Si-Beta, Ti-Beta, Zr-Beta and Fe-Beta.

According to various embodiments described herein, the present invention describes a method for converting glucose into 5-(hydroxymethyl)-furfural (HMF) by contacting a solution comprising glucose with a zeolite selected from the group consisting of Sn-Beta, Si-Beta, Ti-Beta, Zr-Beta and Fe-Beta, wherein the zeolite is made according to the methods described herein.

According to various embodiments described herein, the present invention describes a method for converting xylose into furfural by contacting a solution comprising xylose with a zeolite selected from the group consisting of Sn-Beta, Si-Beta, Ti-Beta, Zr-Beta and Fe-Beta, wherein said zeolite is made according to the methods described herein.

DETAILED DESCRIPTION

The morphology and dispersion status of zeolite seeds in the synthesis gel can substantially affect the crystal growth kinetics of Sn-Beta. By uniformly distributing well-crystalline zeolite beta seeds in the synthesis gel, high-quality Sn-Beta was synthesized in only 2 days with a nearly complete conversion (>90%) of the provided silica source. The Sn-Beta catalyst synthesized by this approach is highly active for the isomerization of triose (C3), pentose (C5) and hexose (C6) sugars.

By "well-crystalline zeolite beta seeds" or "well-crystalline zeolite beta nanocrystals" is meant that zeolite beta nanocrystals (200 nm) seed with high crystallinity. By "high crystallinity" is meant equal to or greater than 80% crystalline. For example, 80%, 81%, 82%, 83%, 84%, 85%, 86% . . . . 95%, 96%, 97%, 98%, 99%, 100%.

Figure 1:
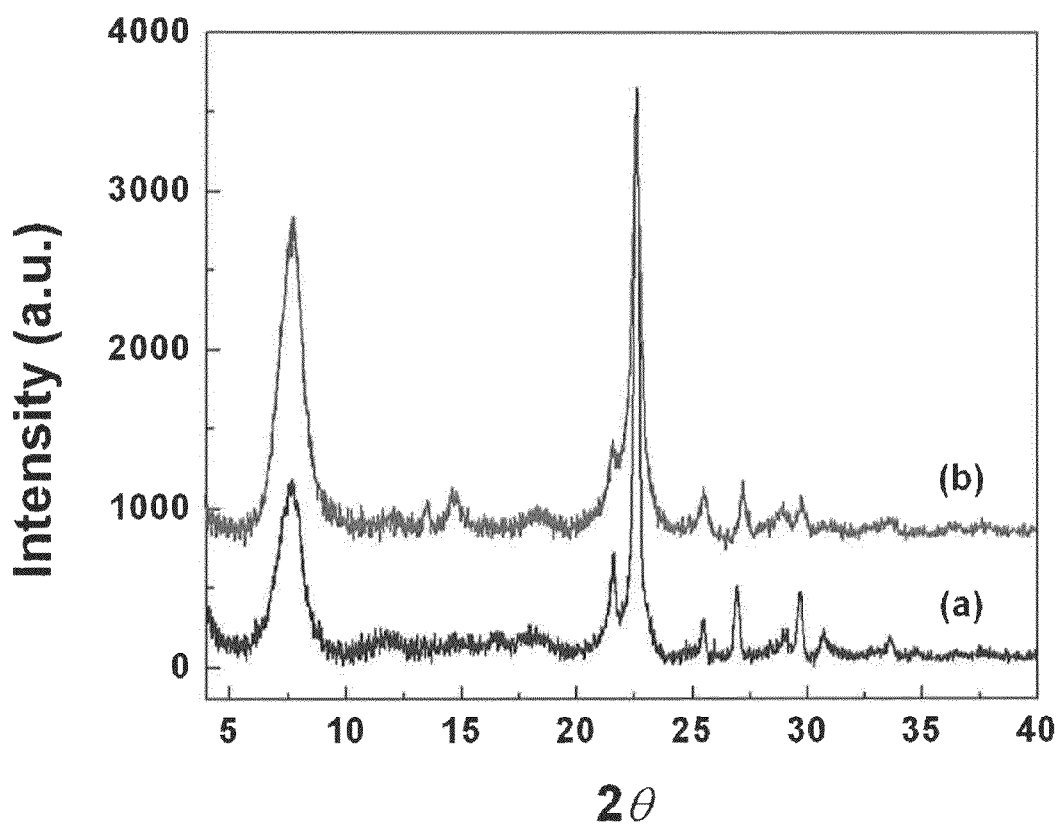
FIG. 1 is XRD patterns of zeolite beta seeds before (a) and after (b) dealumination. XRD pattern (b) is shifted up 800 a.u. for an illustrative reason.

200 nm well-crystalline zeolite beta nanocrystals were used as seeds and added to the synthesis mixture as a suspension. Well-crystalline zeolite beta nanocrystals (Si/Al=23) were prepared according to Mintova et al. (Microporous Mesoporous Mater., 2006, 90:273) and Chen et al. (J. Am. Chem. Soc., 2011, 133:12390). In order to avoid the irreversible aggregation caused by calcination and drying, dealumination of the zeolite seeds was carried out by directly treating the stable seed solution with a concentrated nitric acid solution. The dealuminated zeolite beta seeds were collected by centrifugation and thoroughly washed by deionized water until the pH of the supernatant was below 7. The final concentration of the obtained seed solution was adjusted to 0.145 g/mL by dispersing the seeds in deionized water. During the whole process, no drying or calcination was performed on the sample, which enabled the preparation of a stable suspension with well-dispersed dealuminated zeolite seeds. The crystallinity of the seeds showed no sign of a significant change after the dealumination process as illustrated by the XRD patterns (FIG. 1). After the dealumination no detectable Al was found in the seeds by an elemental analysis. Details of the seed synthesis and the dealumination process can be found in the Examples.

For the synthesis of Sn-Beta, a clear synthesis solution was made by adding tetraethylorthosilicate (TEOS) into tetraethylammonium hydroxide solution (TEAOH). Tin (IV) chloride was first dissolved in deionized water before being added into the prepared clear solution. The resulting solution was stirred in a hood until the ethanol generated from the hydrolysis of TEOS was completely evaporated. Next, HF was added with stirring, and the solution turned into a dry gel at this stage. Finally, the suspension containing dealuminated zeolite seeds (4.1 wt % seeds with respect to the silica content in the dry gel) were directly added into the dry gel and homogenized. The composition of the final gel was $SiO_2$:0.54 TEAOH:0.54 HF:0.008 $SnO_2$:7.5 $H_2O$. The hydrothermal synthesis was carried out in a Teflon-lined stainless steel autoclave at 140° C. with a rotation of 2 rpm. Synthesis details can be found in the Examples.

Figure 2:
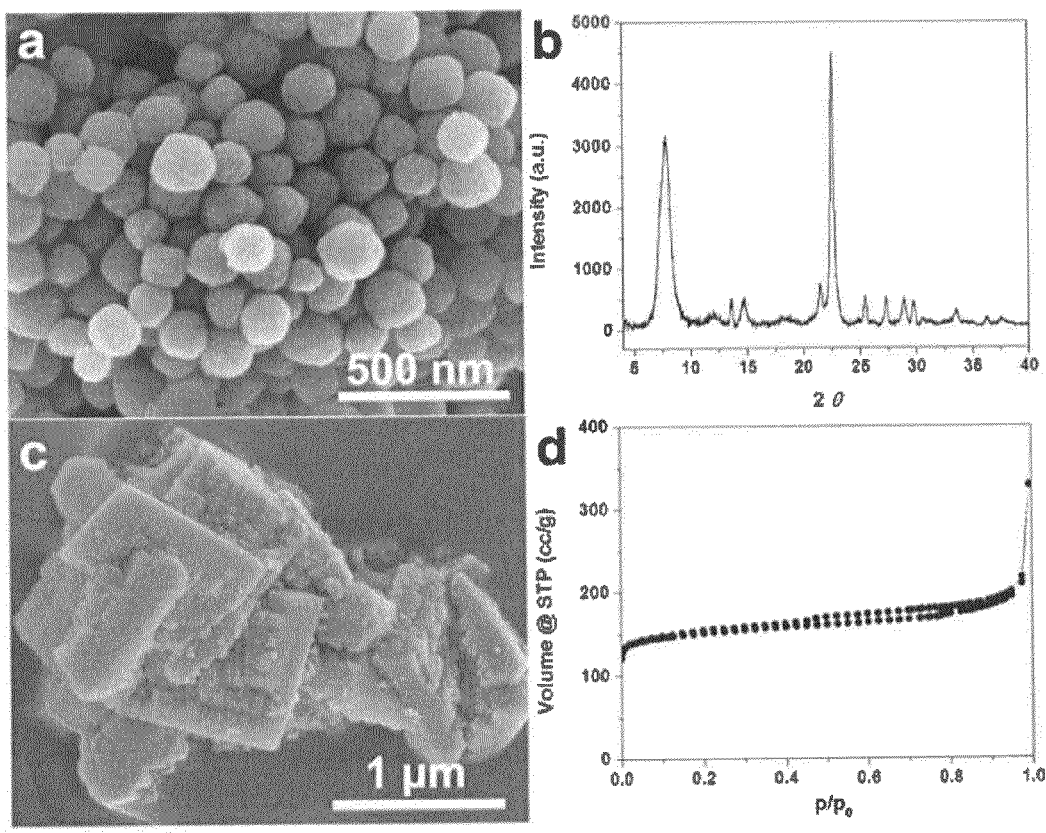
FIG. 2 shows the characterization of zeolite beta seeds and synthesized Sn-Beta. (a) is a SEM image of zeolite beta seeds; (b) is a SEM image (c) is a XRD pattern and (d) is a N2 adsorption/desorption isotherms of the synthesized Sn-Beta (52h)
Figure 3:
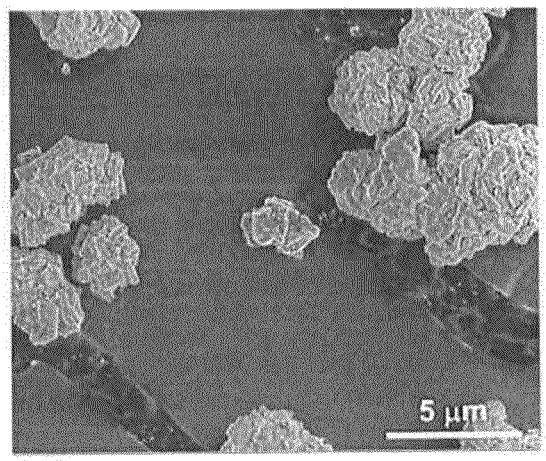
FIGS. 3A and B are SEM images of the synthesized Sn-Beta.
Figure 3:
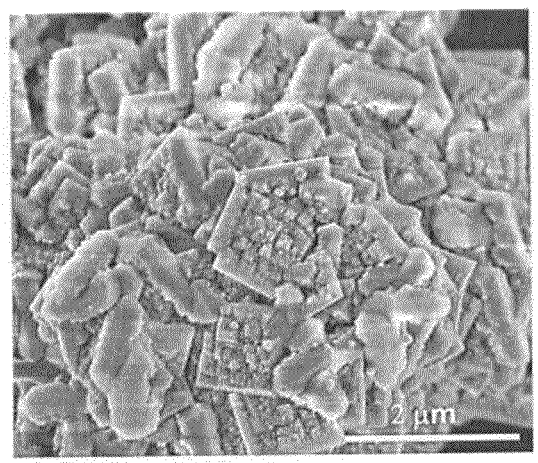
Figure 4:
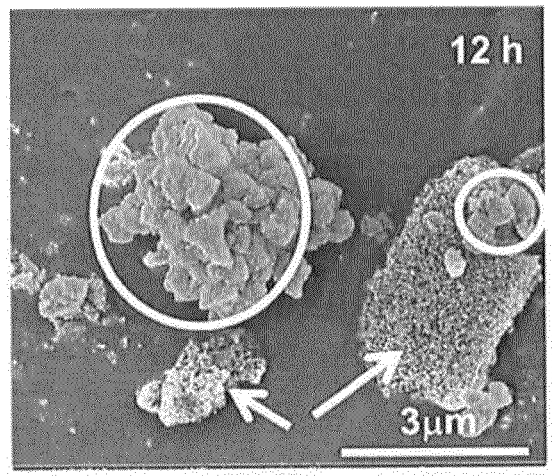
FIG. 4 is SEM images of the products obtained after 12 h (a) and 24 h (b) hydrothermal treatment (arrows indicate the amorphous phase and circles point out the crystals) and the corresponding XRD patterns (c)
Figure 4:
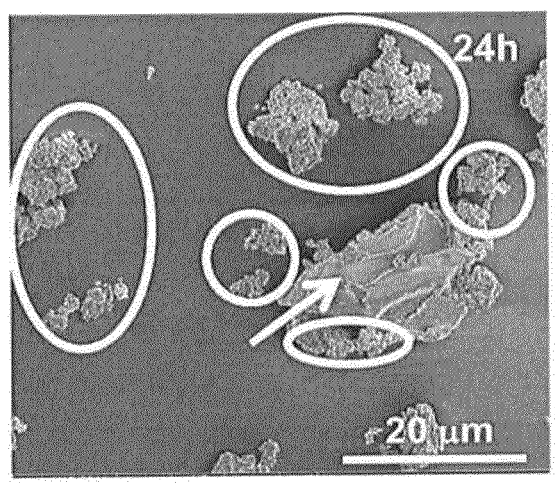
Figure 4:
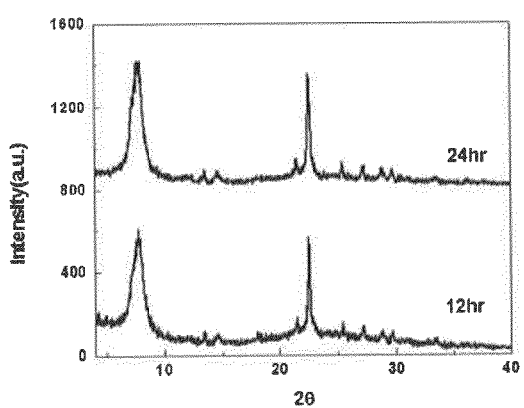
Figure 5:
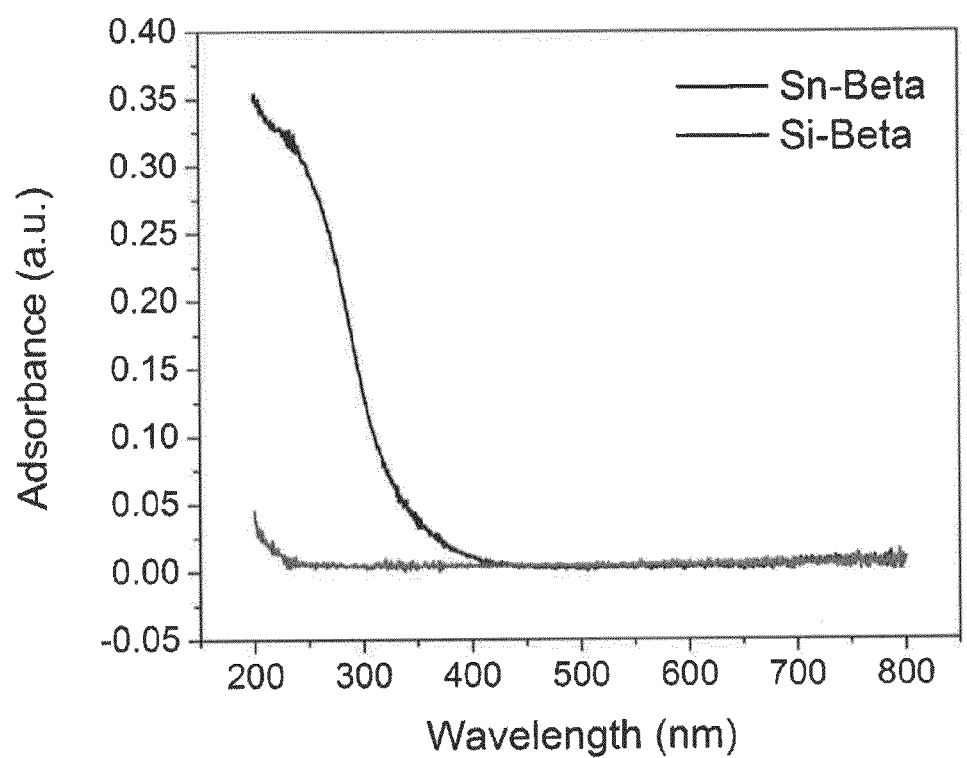
FIG. 5 is UV-Vis diffuse reflectance spectrum of synthesized Sn-Beta and siliceous Beta.
Figure 6:
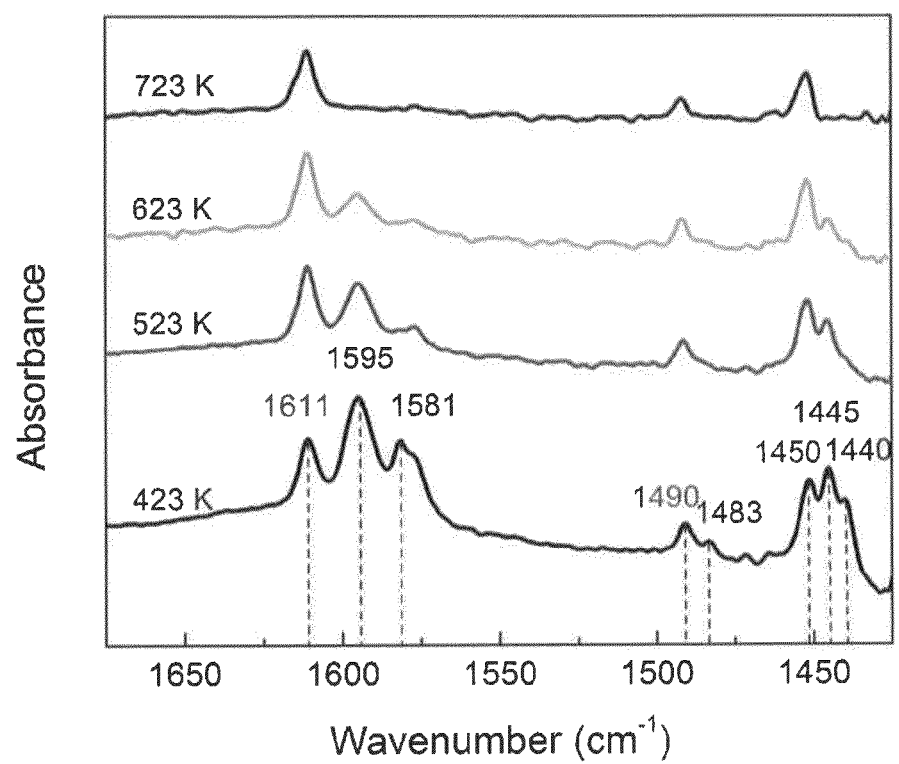
FIG. 6 is IR spectra of Sn-Beta after pyridine adsorption at 393 K for 30 min and desorption at 423 (a), 523 (b), 623 (c), and 723 K (d) for 1 h, respectively. The bands (1611, 1490 and 1450 $cm^{-1}$) associated to Lewis acidity are marked in red.

FIG. 2 reveals the characterization of the zeolite beta seeds and the synthesized Sn-Beta. The SEM image of the zeolite beta indicates the size of the spherical seeds is around 200 nm (FIG. 2a). The XRD pattern (FIG. 2b) indicates that highly crystalline Sn-Beta can be achieved after 52 hours by this approach. The SEM images (FIG. 2c and FIG. 3) reveal that discrete Sn-Beta crystals are highly intergrown. The size of the primary crystal was around 1 μm, and the size of secondary particles ranged from several to tens of μm. Nitrogen sorption measurement of the calcined crystals further confirmed the high crystallinity of the material. The adsorption/desorption isotherms are typical of microporous materials (Type I). The noticeable hysteresis loop located at ~0.5<P/$P_0$<0.8 indicates that mesopores exist in the structure, which could be a result of the highly intergrown structure as shown in the SEM image (FIG. 2c). The calculated micropore volume and BET surface area are 0.19 $cm^3$/g and 488 $m^2$/g, respectively, (Table 1). The yields of the Sn-Beta (calculated from the calcined samples) were consistently above 90% with respect to the amount of $SiO_2$+$SnO_2$ in the synthesis gel when the synthesis time was longer than 52 h. The final Si/Sn ratio of the Sn-Beta made by this method after 52 h was 126 (Table 1). In comparison, the samples collected after 12 h and 24 h were a mixture of crystalline phase and unreacted amorphous phase as indicated by the XRD patterns and SEM images (FIG. 4). UV-Vis spectrum of the Sn-Beta showed absorbance from 200 nm to 250 nm indicating the presence of Sn in the sample, although the coordination status of Sn is not conclusive from the measurement. (FIG. 5). In addition, IR spectra of adsorbed pyridine on the Sn-Beta in the range of pyridine ring-stretching modes were measured to demonstrate the Lewis acidity of the Sn-Beta catalyst. The bands at 1610, 1490, and 1450 $cm^{-1}$ attributed to different vibration modes of pyridine molecule interacting with Sn species within the molecular sieve were observed from the Sn-Beta sample revealing the presence of Lewis acidity in the sample (FIG. 6). These bands remained even after desorption at 723 K indicating the stability of the Lewis acid sites at the relatively high temperature. Due to the high Si/Sn ratio in the Sn-Beta sample (Si/Sn=125, 1.6 wt %) and the complex structure of the zeolite beta topology, $^{119}$Sn MAS NMR measurement on the sample did not show measurable signal rising above the noise, limiting the identification of the coordination environments of Sn in the framework. Further studies on the coordination environments of Sn using $^{119}$Sn enriched reactants are under investigation.

The IR spectra of adsorbed pyridine in the range of pyridine ring-stretching modes on the Sn-Beta were measured after desorption at different temperatures. The vibrations of stretching modes of hydrogen-bonded (hb) and physically (ph) adsorbed pyridine were observed at 1595 cm-1 (hb, mode 8a), 1581 cm-1 (hb, ph, mode 8b), 1483 cm-1 (ph, mode 19b) 1445 cm-1 (hb, mode 19b) and 1440 cm-1 (ph, mode 19b), respectively. The physically adsorbed pyridine (bands at 1483 cm-1 and 1440 cm-1) completely diminished after the desorption at 523 K. Hydrogen-bonded pyridine at 1595 cm-1 and 1445 cm-1 contributed by the hydroxyl groups (from the defects and external surface of the catalyst) decreased in intensity with increasing the desorption temperature. Absorbance at 1550 cm-1 associated with strong Brønsted acid sites was not observed in the sample. In addition to the hydrogen-bonded and physically adsorbed pyridine, the two distinct bands at 1611 cm-1 and 1490 cm-1 and a shoulder one at 1450 cm-1 were observed in all spectra. The bands are associated with the different vibration modes of the pyridine-rings adsorbed on the Sn species within zeolite beta, clearly indicating the presence of Lewis acidity in the sample. The three bands remained even after desorption at 723 K showing the Lewis acid sites are resistant against the relatively high temperature.

Figure 7:
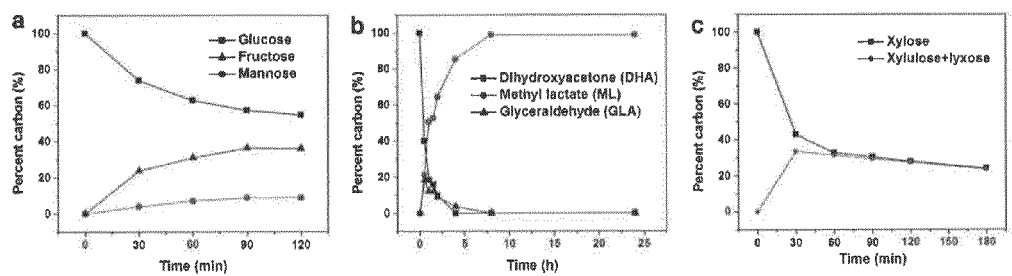
FIG. 7 shows yields of major products as a function of reaction time for the reactions of cellulosic sugars catalyzed by the Sn-Beta. (a), Isomerization of glucose in aqueous phase. Reaction conditions: initial glucose concentration of 10 wt %, glucose to tin molar ratio of 50:1, 100 mg Sn-Beta, 90° C.; (b), Reaction of dihydroxyacetone (DHA) in methanol. Reaction conditions: 1.25 mmol DHA, 4 g methanol, 80 mg Sn-Beta, 70° C.; (c), Isomerization of xylose in aqueous phase. Reaction conditions: initial xylose concentration of 10 wt %, xylose to tin molar ratio of 70:1, 78 mg Sn-Beta, 100° C.
Figure 8:
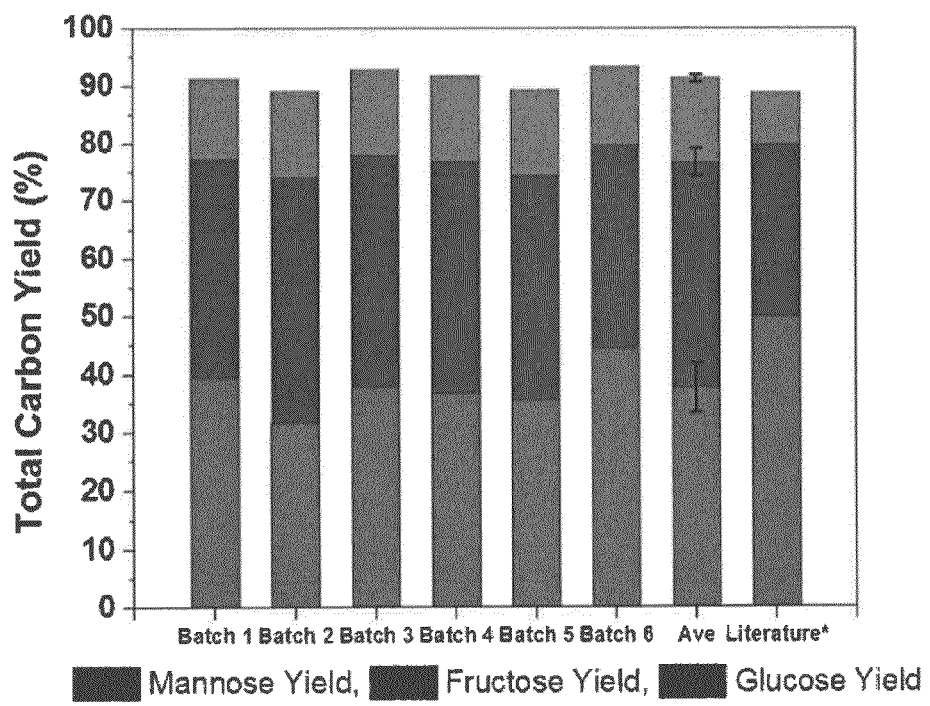
FIG. 8 shows product distribution for the isomerization of glucose using the Sn-Beta synthesized from different batches. Reaction conditions: initial glucose concentration of 10 wt %, glucose to tin molar ratio of 50:1, 100 mg Sn-Beta, 90° C. (Literature data is from the work of Moliner et al., Proc. Natl. Acad. Sci. U.S.A., 2010, 107: 6164-68)

The catalytic performance of the synthesized Sn-Beta was first tested on the isomerization of glucose in aqueous phase at 90° C. The main products of the isomerization are fructose and mannose. The conversion of glucose after 2 h is 54%, the yields of fructose and mannose are 36% and 9%, respectively (FIG. 7). To evaluate the reproducibility of the method of the invention, Sn-Beta made from 6 different batches were tested on the isomerization of glucose. The standard deviation of their activity, an indicator of reproducibility, is less than 4% (FIG. 8).

Sn-Beta catalyst is highly active for the isomerization-esterification of triose sugar to methyl lactate. The Sn-Beta made by the process of the invention was used to catalyze the reaction of dihydroxyacetone (DHA) in methanol at 70° C. (FIG. 7b). As expected, DHA was selectively converted to methyl lactate with a small amount of glyceraldehyde (GLA), an isomer of DHA, in the first hour. After 7 h, DHA was fully converted to methyl lactate.

The catalytic performance of the synthesized Sn-Beta was further tested on the isomerization of xylose, a pentose sugar, in water at 100° C. (FIG. 7c). The products of the reaction are xylulose, lyxose and byproducts from degradation reactions and/or polymerization reactions. The isomerization of xylose to xylulose catalyzed by Sn-Beta is analogous to the isomerization of glucose to fructose. Since the HPLC column used in the analysis cannot separate xylulose and lyxose, the total yields of the two isomers were plotted with the reaction time in FIG. 7c. The isomerization reaction reached equilibrium at 0.5 h with a maximum xylulose+lyxose yield of 35% at xylose conversion of 61%. The xylulose+lyxose yield decreased with time as a result of the side reactions consuming xylose, xylulose and lyxose.

Figure 10:
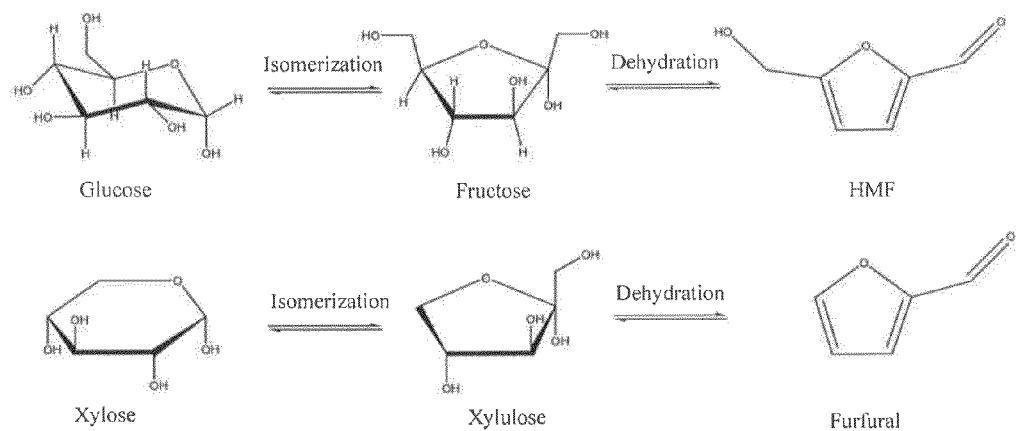
FIG. 10 is a schematic representation of reaction pathway for glucose conversion to HMF (top) and xylose to furfural (bottom)

In addition to isomerization reaction, the Sn-Beta catalyst can also catalyze dehydration reaction. When Sn-Beta is used to catalyze xylose in water, 5% furfural formed from the dehydration of xylose of its isomers is also detected (entry 1 in Table 2). With increasing the reaction time to 12 h, 10% of furfural yield at a xylose conversion of 89% is obtained as shown at entry 2 in Table 2. A biphasic system can improve the furfural yield by in situ extraction of furfural formed during the reaction from aqueous phase to organic phase for directing the reaction equilibrium toward furfural, and preventing undesired degradation and polymerization of furfural. A water/methyl isobutyl ketone (MIBK) biphasic system (entry 3 in Table 2), therefore, was used in this reaction. Compared to single phase system, a much higher furfural yield of 40% is achieved at 150° C. for 90 minutes. The results clearly indicate that the Sn-Beta not only catalyzes the isomerization reaction of xylose to xylulose due to its Lewis acidity, but also facilitates the formation of furfural from a dehydration reaction of xylose or its isomers. A similar result is observed when glucose was used as the reactant; the Sn-Beta produced 40% HMF in a biphasic reaction system at 150° C. for 12 h (entry 4 in Table 2). The scheme of the cascaded reactions is shown in FIG. 10.

Figure 9:
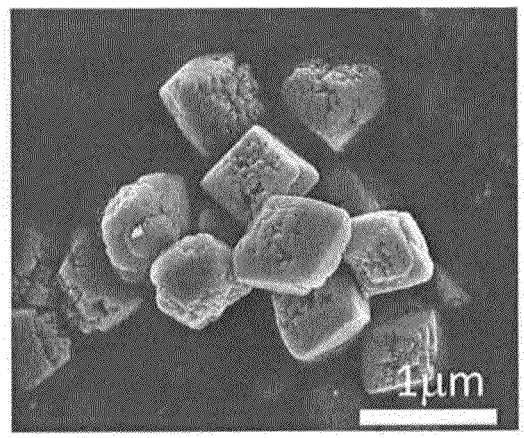
FIG. 9 is SEM images of the siliceous zeolite beta synthesized with (a) and without (b) using a seed solution. Siliceous zeolite beta can be synthesized in 50 h at 140° C. by adding a suspension containing well-crystalline zeolite seeds into the synthesis gel. The crystallization time of siliceous zeolite beta without using the seed solution is 307 h at 140° C.
Figure 9:
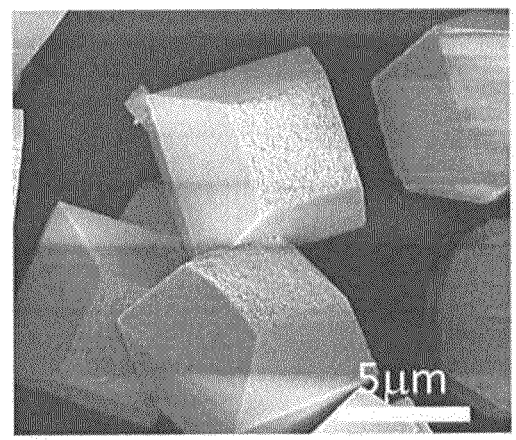

By the methods of the present invention, the crystallization time of Sn-Beta was significantly reduced to two days through a modified seeding method. In the methods of the invention (1) well-crystalline zeolite crystals (200 nm) were used as the seeds, and (2) to avoid the aggregation of the seeds, a stable suspension containing the well-crystalline zeolite seeds was prepared, and directly added into the synthesis mixture without calcination and drying. These two parameters enable the well-crystalline seeds to be uniformly distributed in the synthesis mixture. The crystallization time for Sn-Beta was, thus, effectively shortened. The significantly reduced crystallization time presents an important progress for widespread laboratory and industrial use of Sn-Beta as an active Lewis catalyst. The resulted Sn-Beta catalyzes the isomerization reactions of triose, pentose and hexose sugars. The synthesis method is applicable to other zeolites, like siliceous zeolite beta, Ti-Beta, Zr-Beta, etc. To demonstrate the versatility of the synthesis approach, siliceous zeolite beta was synthesized by the method. It was found that the crystallization time of siliceous zeolite beta can be reduced from 300 h to 50 h (see Examples, FIG. 9).

EXAMPLES

Example 1

Synthesis and Characterization

Preparation of Seed Solution 0.1 g of sodium hydroxide (≥98%, Aldrich) were dissolved in 11.83 g of tetraethylammonium hydroxide solution (TEAOH, 35%, Alfa Aesar), followed by drop wise adding 17.85 g of Ludox HS-30 colloidal silica (30%, Aldrich). After dissolving LUDOX HS-30 at room temperature, 0.365 g of aluminum isopropoxide (Aldrich) were added into the solution. The composition of the solution was 25 $SiO_2$:0.25 $Al_2O_3$:9 TEAOH:0.35 $Na_2O$:331 $H_2O$. The mixture was aged for 1 day at room temperature and filtered with a 200 nm syringe filter to obtain a clear solution. The clear solution was charged into a Teflon-lined stainless steel autoclave, and heated at 100° C. for 7 days in a preheated oven. The formed zeolite nanocrystals were collected by centrifugation and repeatedly washed by deionized water until the pH is blow 7. Finally, the aluminosilicate zeolite beta nanocrystals were re-dispersed into deionized water without drying. The crystal concentration in the suspension was 0.145 g/mL. Dealumination of the crystals was achieved by treating 2.5 mL of the suspension with 25 mL of concentrated nitric acid (69%, Fisher) in a Teflon-lined stainless steel autoclave at 80° C. for 24 h. The dealuminated zeolite beta was collected by centrifugation and thoroughly washed by deionized water until the supernatant approached a neutral pH. The obtained products were then re-dispersed into deionized water by sonication without drying. The final crystal concentration in the suspension was 0.145 g/mL.

Synthesis of Sn-Beta

In a typical run, 6.98 g of tetraethylorthosilicate (TEOS, Alfa Aesar, 98%) were added into 7.67 g of tetraethylammonium hydroxide solution (TEAOH, Alfa Aesar, 35%), and stirred at room temperature until it became a homogeneous solution (about 1 h to 1.5 h). Then, 0.1 g of tin chloride (Alfa Aesar) were dissolved in 0.64 g of deionized water. These two solutions were mixed together, and stirred in a hood until the ethanol generated from the hydrolysis of TEOS was completely evaporated. The final weight loss was 7.99 g (6.04 g of ethanol and 1.95 g of water). Then, 0.74 g of hydrofluoric acid (Alfa Aesar, 48%) were added into the solution with stirring. Finally, 0.579 mL of dealuminated zeolite beta seed solution (0.145 g/mL) were added into the solution (4.1 wt % with respect to the silica content), and homogenized with a plastic spatula. The composition of the final gel was $SiO_2$:0.54 TEAOH:0.54 HF:0.008 $SnO_2$:7.5 $H_2O$. The obtained gel was then loaded into a Teflon-lined stainless steel autoclave, and heated at 140° C. with a rotation of 2 rpm for various times. The product was filtered and thoroughly washed by deionized water, and dried in a 100° C. oven overnight. The obtained solid was calcined with a ramping rate of 1° C./min to 550° C. for 12 h to remove the organic structure directing agent and fluoride ions.

Synthesis of Siliceous Zeolite Beta

Siliceous zeolite beta was prepared by seeded growth method using the seed solution prepared with the method described above. The synthesis gel for the seeded growth was prepared according to the literature method (Larlus and Valtchev, Chem. Mater., 2005, 17:881-6). First, 1.04 g of hydrofluoric acid were added into 10.52 g of 35% TEAOH solution. Then, 3 g of fumed silica (CAB-O-SIL M-5, Cabot) were slowly added into the solution and mixed with stirring. The composition of the gel was $SiO_2$:0.5TEAOH:0.5HF:7$H_2O$. Finally, 0.331 mL dealuminated zeolite beta seed solution (0.145 g/mL) was added into the gel (1.6 wt % with respect to silica content in synthesis gel), and homogenized by stirring with a plastic spatula. The resulting gel was charged into a Teflon-lined stainless steel autoclave and reacted at 140° C. for various times. The product was centrifuged, washed by deionized water, and dried in a 70° C. oven. The yield was calculated based on the silica amount in the initial gel and the weight of crystals after the removal of the organic structure directing agent (1° C./min, 550° C. for 12 h). Siliceous zeolite beta was also made without adding the seed solution into the synthesis gel.

Characterizations

The crystalline phase of the Sn-Beta was examined by using an XRD diffractometer (X'pert Pro, PANalytical) operated at an acceleration voltage of 45 kV and a current of 40 mA. The morphology of the product was investigated by using a scanning electron microscope (Magellan 400, FEI) with Pt coating. The nitrogen adsorption-desorption isotherm was collected on an automated gas sorption analyzer (Autosorb iQ, Quantachrome) after degassed at 200° C. under vacuum. Chemical analysis of the sample was performed on an inductively coupled plasma-optical emission spectrometer (iCap 6500 dual view, Thermo Scientific). The FT-IR spectrum was collected on an FT-IR spectrometer (Equinox 55, Bruker) in absorbance mode at a spectral resolution of 2 cm$^{-1}$ with the Praying Mantis™ High Temperature Reaction Chamber (Harrick). The sample was heated at 823K for 1 h. The pyridine adsorption was carried out by exposing the pretreated sample to a pyridine vapor at 393 K for 30 min and followed by He flow for 1 h to remove weakly adsorbed and residue species in the chamber. The adsorbed pyridine was desorbed successively at different temperatures (423 K, 523 K, 623 K and 723 K) for h. All the spectra were collected at 393 K.

TABLE 1

Textual analysis and elemental analysis of Sn-Beta.

| | Micropore volume (cc/g)$^a$ | Micropore volume (cc/g)$^b$ | External surface area (m$^2$/g)$^b$ | BET surface area (m$^2$/g)$^c$ | Total pore Volume (cc/g)$^d$ | Si/Sn$^e$ |
|---|---|---|---|---|---|---|
| Sn-Beta | 0.188 | 0.176 | 131 | 488 | 0.32 | 126 |

$^a$From t-plot method;
$^b$From α$_t$-plot method;
$^c$Calculated from P/P$_0$ range of 0.05-0.25 using BET equation;
$^d$Calculated from amount absorbed at P/P$_0$ = 0.975;
$^e$ICP-OES.

Example 2

Catalytic Tests

All the chemicals (xylose, glucose, dihydroxyacetone dimer and methanol) used in the reactions were purchased from Sigma-Aldrich.

Isomerization of Glucose

A glucose isomerization reaction was used to test the catalytic activity of the synthesized Sn-Beta catalyst. The reaction was performed according to the work of Moliner et al. (Proc. Natl. Acad. Sci. USA, 2010, 107:6164-68). Sn-Beta was added at a 1:50 Sn:glucose molar ratio to a 10 wt % glucose solution in a 3 mL thick-walled glass reactor. The reaction vial was placed in a temperature-controlled aluminum heating block set to 90° C. with 500 rpm stirring. After reaction for various times, the glass reactors were quenched in ice for 15 min, dried, and weighed before opening to make sure there was no leaking during the reaction.

Isomerization of Xylose

The isomerization of xylose was performed according to the work of Choudhary et al. (ACS Catal., 2011, 1:1724-28). Sn-Beta was added at a 1:70 Sn:xylose molar ratio to a 10 wt % xylose solution in a 3 mL thick-walled glass reactor. The reaction vial was placed in a temperature-controlled aluminum heating block set to 100° C. with 500 rpm stirring. After reaction for various times, the glass reactors were quenched in ice for 15 min, dried, and weighed before opening to make sure no leaking occurred during the reaction.

Conversion of Dihydroxyacetone (DHA) to Methyl Lactate (ML)

Conversion of dihydroxyacetone (DHA) to methyl lactate (ML) in methanol was performed according to the work of Taarning et al. (Chem Sus Chem, 2009, 2:625-27). In a typical experiment, 1.25 mmol of DHA. 4 g methanol and 80 mg Sn-Beta were added to a 3 mL thick-walled glass reactor. The reactor was placed in temperature-controlled aluminum heating block set to 70° C. with 500 rpm stirring. After reaction for various times, the glass reactors were quenched in ice for 15 min, dried, and weighed before opening to make sure no leaking occurred during the reaction.

Isomerization/Dehydration of Xylose

Sn-Beta was added at a 1:70 Sn:xylose molar ratio to a 1 ml 10 wt % xylose solution in a 20 ml thick-walled glass reactor. 3 ml methyl isobutyl ketone was added in the reactor as an extraction phase to protect the formed furfural. The reaction vial was placed in a temperature-controlled oil bath set to 150° C. with 500 rpm stirring. After reacting for 1.5 h, the glass reactors were quenched in ice for 15 min, dried, and weighed before opening to make sure no leaking occurred during the reaction. The concentration of the reactants and products in water phase and organic phase were measured, respectively.

Isomerization/Dehydration of Glucose

Sn-Beta was added at a 1:50 Sn:glucose molar ratio to a 1 ml 10 wt % glucose solution in a 20 ml thick-walled glass reactor. 3 ml methyl isobutyl ketone was added in the reactor as an extraction phase to protect the formed HMF. The reaction vial was placed in a temperature-controlled oil bath set to 150° C. with 500 rpm stirring. After reacting for 6 h, the glass reactors were quenched in ice for 15 min, dried, and weighed before opening to make sure no leaking occurred during the reaction. The concentration of the reactants and products in water phase and organic phase were measured, respectively.

Sample Analyses

For the reactions with pentose and hexose, sample analyses were performed using liquid chromatography (Shimadzu LC-20AT). Sugars were detected with a RI detector (RID-IOA), and other products were detected with a UV-Vis detector (SPD-20AV) at wavelengths of 210 and 254 nm. The HPLC column used was a BIO-RAD HPX-87H sugar column. The mobile phase was 0.005 M 1H$_2$SO$_4$ flowing at a rate of 0.6 mL/min. The column oven was set to 30° C. The column can efficiently separate the isomers of C6 sugar, such as glucose, fructose and mannose, but shows poor separation for xylulose (10.118 min) and lyxose (10.175 min). It was found that the response factors of xylulose and lyxose on the RI detector are similar (difference is less than 20%). The combined yield of xylulose and lyxose were, thus, calculated from the peak with a retention time from 10.1 min to 10.2 min.

DHA and ML were detected on an Agilent 6890 gas chromatography equipped with an IFID-detector and a Restek RTX-VMS capillary column (30.0 m/0.25 mm id/1.4 µm film thickness). A helium flow rate of 6.0 mL/min pressurized at 1.498 bar was used. The oven temperature program is as follows: the initial temperature is 50° C. (hold 2 min) and then heated to 240° C. (ramp 20° C./min, hold 20 min).

Conversion and yield are defined as follows:

$$\text{Conversion}_{glucose} = (\text{moles}_{glucose\ reacted})/(\text{moles}_{glucose\ initial})$$

$$\text{Conversion}_{DHA} = (\text{moles}_{DHA\ reacted})/(\text{moles}_{DHA\ initial})$$

$$\text{Conversion}_{xylose} = (\text{moles}_{xylose\ reacted})/(\text{moles}_{xylose\ initial})$$

$Yield_{glucose} = (moles_{glucose})/(moles_{glucose\ initial})$ $Yield_{fructose} = (moles_{fructose\ produced})/(moles_{glucose\ initial})$ $Yield_{mannose} = (moles_{mannose\ produced})/(moles_{glucose\ initial})$ $Yield_{xylulose+lyxose} = (moles_{xylulose+lyxose\ produced})/(moles_{xylose\ initial})$ $Yield_{ML} = (moles_{ML\ produced})/(moles_{DHA\ initial})$

TABLE 2

Results of conversion of xylose to furfural and glucose to HMF using Sn-Beta.

| Entry | System | Catalyst | Conv. [%] | Furfural yield [%] | Time [min] | Temp. [° C.] |
|---|---|---|---|---|---|---|
| 1 | Single Phase (H₂O) xylose | Sn-Beta | 81 | 5 | 180 | 100 |
| 2 | Single Phase (H₂O) xylose | Sn-Beta | 89 | 10 | 720 | 100 |
| 3 | Biphasic (H₂O/MIBK) xylose | Sn-Beta | 98 | 40 | 90 | 150 |
| 4 | Biphasic (H2O/MIBK) glucose | Sn-Beta | 98 | 40 (HMF) | 720 | 150 |

Reaction conditions: Initial xylose 10 wt % in water, xylose to tin molar ratio of 70:1. Entry 3: aqueous to organic phase ratio of 1:3 in volume. Entry 4: aqueous to organic phase ratio of 1:3 in volume. Initial glucose 10 wt % in water, glucose to tin molar ratio of 50:1.

The results shown in Table 2 above indicate that the Sn-Beta catalyst can catalyze both isomerization reaction and dehydration reaction together. It acts as a bifunctional catalyst for "one-pot" synthesis of 5-(hydroxymethyl)-furfural and furfural from glucose and xylose, respectively. This "one-pot" synthesis using only the heterogeneous catalysts of the present invention presents clear advantages to current industrial approaches where liquid acids are used. The advantages include ease of catalyst separation, simplicity and versatility of process engineering, and reduced reactor and plant corrosions.

Example 3

Figure 11:
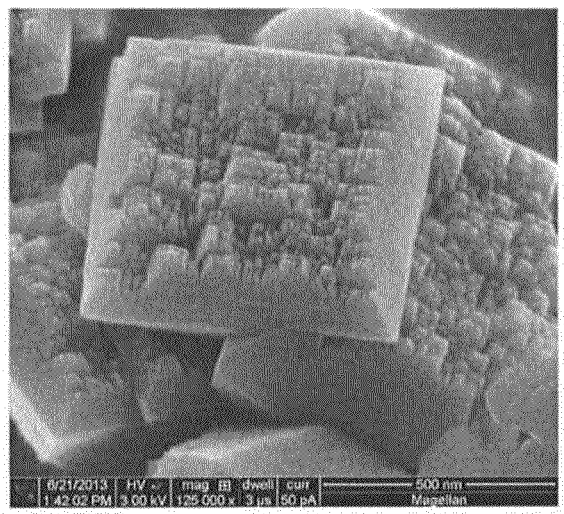
FIG. 11 is (a) SEM and (b) XRD data of the Sn-Beta synthesized at 200° C. in 6 hours.
Figure 11:
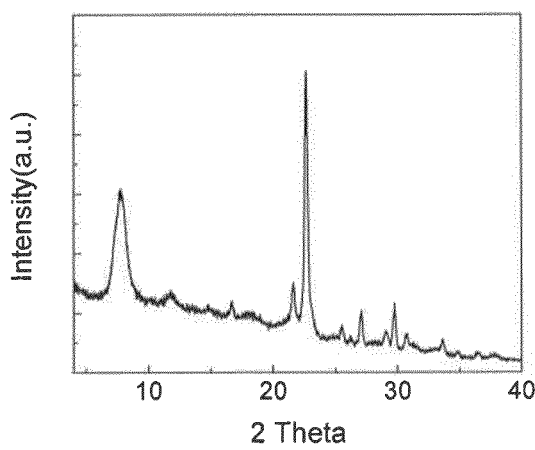

Reducing Crystallization Time to 6 Hours by Increasing Crystallization Temperature Using the same compounds and sample preparation method as described above in Example 1, the crystallization time for the synthesis of hydrophobic Sn-Beta has been further reduced to 6 hours by increasing the reaction temperature. Fully crystalline Sn-Beta zeolite was obtained in 12 hours and 6 hours when the synthesis temperature is 175° C. and 200° C., respectively. The significantly enhanced crystallization rate is ascribed to the well dispersed beta zeolite seeds with high crystallinity as observed in Example 1. The structure directing agent (SDA) used in the synthesis is tetraethylammonium hydroxide (TEAOH). In the synthesis system, Hofmann elimination reactions of TEAOH forming lighter amines is avoided since the pH of the synthesis solution is close to neutral. The crystallization temperature was increased from 140° C. to 200° C. High-quality Sn-Beta was achieved in 6 hours. FIG. 11 shows the XRD pattern and SEM image of the Sn-Beta synthesized at 200° C. in 6 hours. The catalytic activity of the Sn-Beta is similar to the one synthesized in 2 days with a crystallization temperature of 140° C. as shown in Table 3.

TABLE 3

Catalytic activity of Sn-Beta synthesized 200° C. in 6 hours and comparison with Sn-Beta synthesized at 140° C. in 2 days.

| 10 wt. % glucose in water; 95° C.; 15 min | Glucose yield (%) | Fructose + Mannose yield (%) |
|---|---|---|
| 200° C. 6 hours | 73.3 | 24.4 |
| 140° C. 2 days | 72.0 | 27.4 |

Example 4

Synthesis of Sn-Beta with NH₄F

Compared to HF, NH₄F is a safe fluoride source since NH₄F has a much higher boiling point then HF. Replacing HF with HF also leads to the formation of highly crystalline Sn-Beta.

Synthesis Procedure

In a typical run, 5.58 g of tetraethylorthosilicate (TEOS, Alfa Aesar, 98%) was added into 6.14 g of tetraethylammonium hydroxide solution (TEAOH, Alfa Aesar, 35 wt %), and stirred at room temperature until it became a homogeneous solution (about 1.5 h). Then, 0.08 g of hydrated tin chloride (Alfa Aesar) dissolved in 0.51 g of deionized water was added. The solution was stirred in a hood until ethanol generated from the hydrolysis of TEOS was completely evaporated. The final weight loss was 6.36 g (4.83 g of ethanol and 1.53 g of water). Then, 0.440 mL of dealuminated zeolite beta seed solution (0.152 g/mL) was added into the solution (4.1 wt % with respect to the silica content), and homogenized by using a plastic spatula. Finally 0.55 g of ammonium fluoride (NH₄F, Alfa Aesar, 96%) in 1.13 g of DI was added into the solution with stirring. The composition of the final gel was SiO₂:0.54TEAOH:0.54NH₄F:0.008SnO₂:7.5H₂O. The obtained precursor was then loaded into a Teflon-lined stainless steel autoclave. The autoclave was heated at 140° C. with a rotation of 2 rpm for 4 days. The product was filtered and thoroughly washed by deionized water, and dried in a 100° C. oven overnight. The as-made solid was calcined with a ramping rate of 1° C./min to 550° C. for 12 h to remove the organic structure directing agent and fluoride ions.

Figure 12:
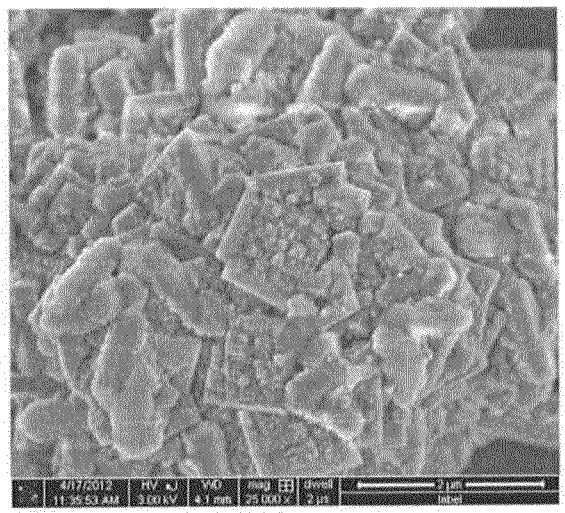
FIG. 12 is (a) SEM and (b) XRD data of the Sn-Beta synthesized in the presence of $NH_4F$ at 140° C. in 4 days.
Figure 12:
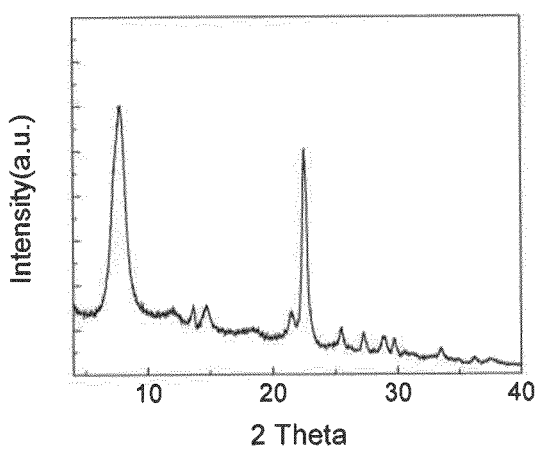

FIG. 12 shows the XRD pattern and SEM image of the Sn-Beta synthesized in the presence of NH₄F at 140° C. in 4 days. The catalytic activity of this Sn-Beta is listed in Table 4.

TABLE 4

Catalytic activity of Sn-Beta synthesized in the presence of NH₄F at 140° C. in 4 days and comparison with Sn-Beta synthesized in the presence of HF at 140° C. in 2 days. The Sn/glucose ratio in the reaction is 50.

| 10 wt % glucose in water; 95° C.; 2 hr | Glucose yield (%) | Fructose + Mannose yield (%) |
|---|---|---|
| NH₄F; 140° C. 4 d | 36 | 48.4 |
| HF; 140° C. 2 d | 37.7 | 53.6 |

Example 5

Fluorine-Free Synthesis of Sn-Beta Zeolite

Although Sn-Beta shows intriguing catalytic properties, the typical synthesis of Sn-Beta, which usually involves utilization of toxic hydrofluoric acid and lengthy synthesis time, has been hampering the detailed study of the material and its potential for use in catalyzing reactions prior to the current invention. Recently, efforts were made to improve the process by using less toxic chemical and modified seeding method, but a fluoride medium was still used. Here, for the first time, a fluorine-free synthesis route for Sn-Beta is disclosed, and the obtained nano-crystalline microporous material is catalytically comparable to conventional Sn-beta, as tested by sugar isomerization reactions. The synthetic method revealed herein is a safer alternative for producing Sn-Beta zeolite.

Sn-Beta zeolite was synthesized from fluoride-free, caustic medium by a seeded dry-gel conversion method. It is shown that the catalytic activity for isomerization reaction of dihydroxylacetone (DHA) in methanol is comparable to conventionally-synthesized Sn-Beta.

The term "caustic medium" means a basic aqueous solution made with NaOH, KOH etc. having a pH from about 9 to about 13.

Sn-Beta (Sn-BEA) zeolite, a crystalline stannosilicate with BEA topology, exhibits discrete Lewis acidity and can catalyze reactions such as Baeyer-Villiger oxidation and Meerwein-Ponndorf-Verley and Oppenauer reaction with superior activity and selectivity. The successful isomerization of glucose to fructose using Sn-Beta zeolite, a reaction highlighted as an key intermediate step in biomass conversion to chemical and fuels has been reported. The inorganic catalyst was then shown to be able to produce 5-(hydroxymethyl)furfural (HMF), an important biomass-derived platform molecule, in a one-pot process by further dehydration of fructose. Moreover, Sn-Beta can also catalyze isomerization of pentose and triose sugars to form key building blocks in chemical industry including furfural, methyl lactate, and lactic acid. Although the tin containing molecular sieve shows intriguing catalytic properties, the typical synthesis of Sn-Beta, which usually involves utilization of toxic hydrofluoric acid and lengthy synthesis time, has been hampering the detailed study of the material and its potential use in catalyzing reactions. Recently, efforts were made to improve the process by using less toxic chemical and modified seeding method, but a fluoride medium was still used. Here a fluorine-free synthesis route for Sn-Beta is disclosed, and the obtained nano-crystalline microporous material is catalytically comparable to conventionally-synthesized Sn-beta, as tested by sugar isomerization reactions. The synthetic method disclosed herein is a safer alternative way for producing Sn-Beta zeolite.

Before fumed silica was added, sodium hydroxide was dissolved in tetraethylammonium hydroxide solution. Tin source solution containing tin butoxide and hydrogen peroxide was added into the above solution, and the resulting solution was stirred for 2 hrs. Suspended heated uncovered in an 80° C. oil bath with stirring for 24 hrs to evaporate the water. The composition of the dry gel was $SiO_2:0.008SnO_2:0.22TEA_2O:0.034\ Na_2O$. The obtained solid (ca. 2 g) was ground into fine powder and put in a Teflon-lined stainless steel autoclave. 0.5 g of deionized water was added into the autoclave in a separate container to avoid direct contact with the powder precursor. The autoclave was then heated in 140° C. oven for 5 days. The as-made sample was washed by filtration with L deionized water and dried in 100° C. oven overnight. Ion-exchange was carried out by treating 0.5 g of as-made zeolite with 25 mL of 1 M ammonium nitrate solution for 2. The process was repeated 5 times. Removal of organic template was done by calcining the powder in a muffle furnace at 550° C. for 12 hrs with a ramping rate of 1° C./min.

Figure 13:
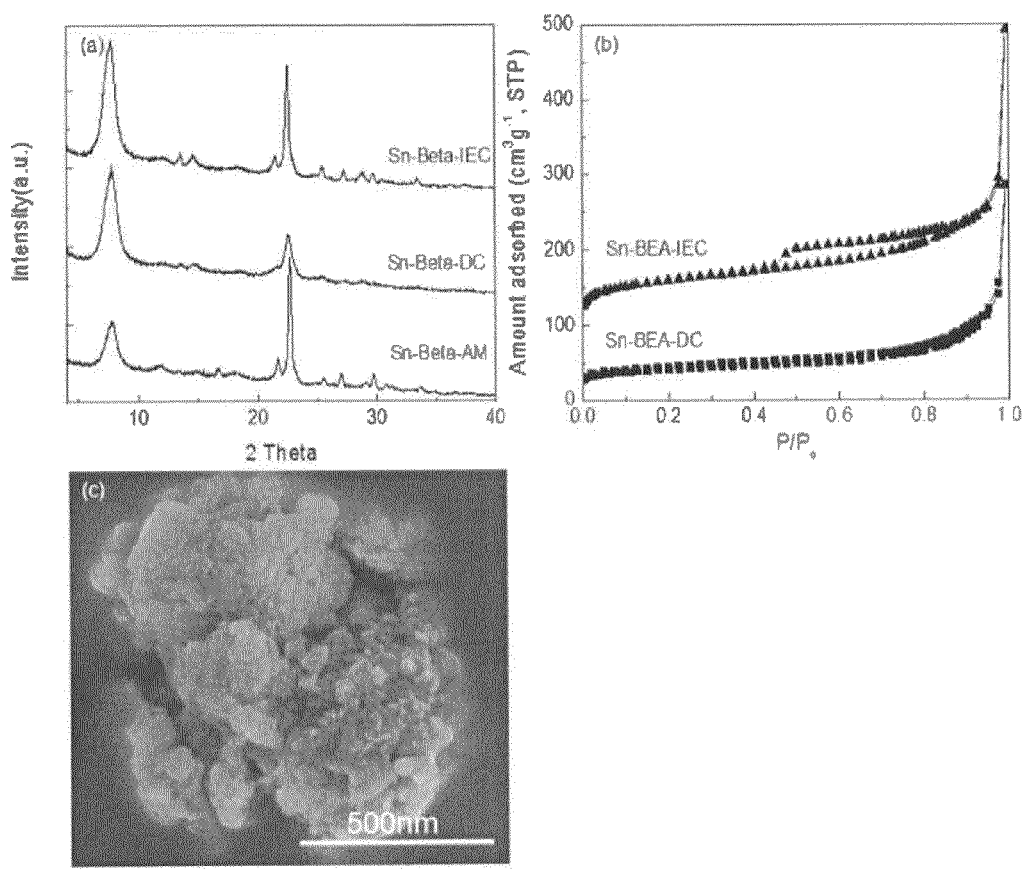
FIG. 13 is (a) PXRD patterns of Sn-BEA-AM, Sn-BEA-DC, and Sn-BEA-IEC, (b) nitrogen sorption isotherms for Sn-BEA_DC and Sn-BEA-IEC, and (c) SEM image of Sn-BEA-IEC.

FIG. 13 shows the powder x-ray diffraction (PXRD) patterns, SEM images, and nitrogen adsorption-desorption isotherm at 77K for Sn-BEA synthesized by this method. FIG. 13(a) reveals the PXRD spectra for as-made (Sn-BEA-AM), direct calcined (Sn-BEA-DC), and calicined after ion-exchanged samples (Sn-BEA-IEC). All samples show the typical reflections corresponding to zeolite BEA phase without other crystalline phases. Sn-BEA-DC sample lost part of crystallinity during the course of calcination, while Sn-BEA-IEC exhibits high crystallinity. While not intending to be held to theory, the partially collapsed structure was attributed to inherent defects on the crystals or those generating for balance the electron density from $TEA^+$ ion ($\equiv$SiO—) were balanced by $Na^+$, which existed in the synthetic solution. The $\equiv$Si—O—Na could not undergo condensation with adjacent defect sites like $\equiv$Si—O—H to form $\equiv$Si—O—Si$\equiv$, so the crystal structure could not be maintained and collapsed. On the other hand, if the Sn-BEA-AM sample was ion-exchanged with $NH_4NO_3$ solution before calcination, the $Na^+$ ion can be replaced by $NH_4^+$ ion. Upon further treatment, $\equiv$Si—O—$NH_4$ would be transformed into $\equiv$Si—O—H, and the subsequent dehydration could occur. The $\equiv$Si—O—Si$\equiv$ bonding thus formed, and the crystallinity and microporous structure of Sn-BEA-IEC could be maintained. Nitrogen sorption isotherms (FIG. 13(b)) also supports the high quality of Sn-BEA-IEC sample ($V_{mic}$=0.177 $cm^3g^{-1}$), whereas Sn-BEA-DC possessed limited amount of accessible micropores (($V_{mic}$=0.033 $cm^3g^{-1}$), which might be due to the destruction of crystal structure. Additionally, the hysteresis loop appearing on the Sn-BEA-IEC sample from $P/P_0$~0.5 indicates the existence of mesopores. It might result from the surface roughness and/or the voids created from drying/crystallization, as shown in the SEM image (FIG. 13(c)). The data indicate that the ion exchange treatment is crucial for obtaining highly crystalline Sn-Beta in the sodium containing steam-assisted crystallization method.

Figure 14:
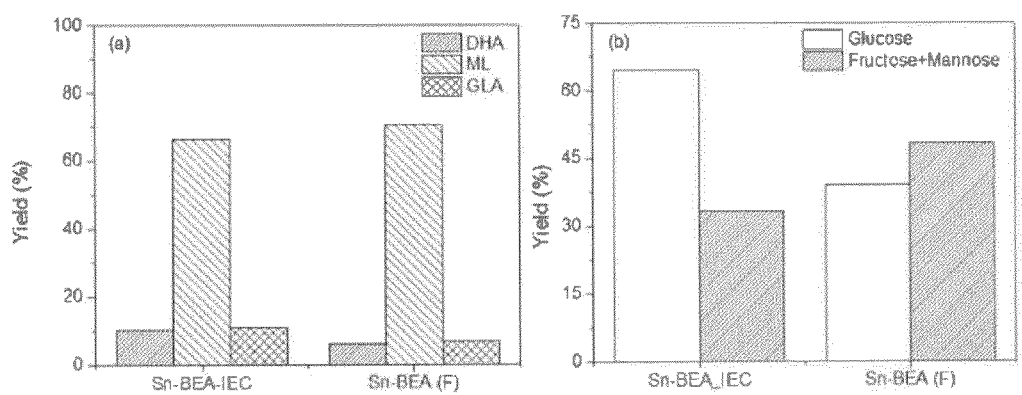
FIG. 14 is bar graphs of (a) Dihydroxyacetone in methanol and (b) glucose isomerization reaction results for Sn-BEA-IEC and Sn-BEA (F), (ML: methyl lactate; GLA: glyceraldehyde)
Figure 15:
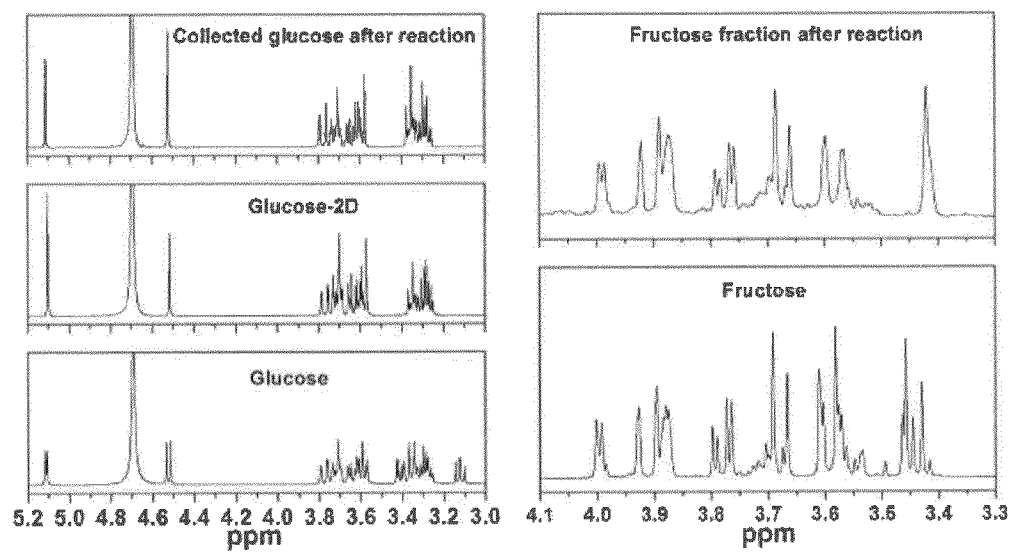
FIG. 15 is an $^1$H-NMR spectrum of fructose after isomerization reaction of deuterium substituted glucose over Sn-BEA-IEC.

The catalytic activity of the Sn-BEA-IEC sample was examined by glucose isomerization in water and dihydroxyacetone (DHA) reaction in methanol, compared with Sn-Beta made from fluoride method (designated as Sn-BEA (F)). As seen in FIG. 14 (a), the reactivity of the Sn-BEA obtained from the current method is comparable to that from fluorine system. After 2 hrs reaction at 70° C., the conversion of DHA reaches over 90%, and yield of methyl lactate (ML) is about 70%. However, in glucose isomerization reaction, the fluorine-free Sn-BEA shows only ~60% activity of Sn-BEA (F). Although not intending to be held to theory, it is believed that the hydrophobic environment is a key factor for adsorption of saccharides in zeolites. Because the charge of occluded $TEA^+$ ion must be compensated either by framework defects ($\equiv$Si—$O^-$) or by other ions (such as $F^-$), the Sn-BEA synthesized as disclosed herein, which is made from caustic medium, is supposed to have more defects than Sn-BEA (F). After ion-exchange and calcination, Sn-BEA-IEC may contain more silanol groups ($\equiv$Si—OH) than Sn-BEA (F) does, and thus behave less hydrophobic and less active in glucose isomerization reaction due to impaired adsorption of glucose.

To confirm the reaction mechanism and Sn coordination environment, deuterium substituted glucose at the C-2 position was used in an isomerization reaction. The absent resonance at δ=3.45 ppm in 1H NMR spectrum of fructose after reaction indicates that the reaction undergoes an intramolecular hydride shift, which follows the same mechanism as conventional Sn-BEA (F), rather than proton transfer for the basic catalysts. Additionally, only framework-substituted Sn can catalyse the reaction through the hydride shift mechanism, whereas octahedrally coordinated tin or extraframework species cannot catalyse the reaction. Thus, the material synthesized herein possesses tetrahedrally coordinated tin in the high silica zeolite BEA framework, and the isolated metal centers exhibit Lewis acidity.

Highly crystalline Sn-Beta was successfully synthesized from caustic medium by a steam-assisted crystallization method. The reaction results show that the activity of the molecular sieve is comparable to conventionally-synthesized Sn-Beta in DHA in methanol reaction, while it reveals lower activity in glucose isomerization reaction, which may be due to the degree of hydrophobicity of the sample. The catalytic identity between the fluorine-free and fluorine mediated Sn-Beta is confirmed by 1H-NMR experiment.

Catalytic Tests

All the chemicals (xylose, glucose, dihydroxyacetone dimer and methanol) used in the reactions were purchased from Sigma-Aldrich.

Isomerization of Glucose

A glucose isomerization reaction was used to test the catalytic activity of the synthesized Sn-Beta catalyst. The reaction was performed according to the work of Moliner et al.[1] Sn-Beta was added at a 1:50 Sn:glucose molar ratio to a 10 wt % glucose solution in a 3 mL thick-walled glass reactor. The reaction vial was placed in a temperature-controlled aluminum heating block set to 90° C. with 500 rpm stirring. After reaction for various times, the glass reactors were quenched in ice for 15 min, dried, and weighed before opening to make sure no leaking during the reaction.

Conversion of Dihydroxyacetone (DHA) to Methyl Lactate (ML)

Conversion of dihydroxyacetone (DHA) to methyl lactate (ML) in methanol was performed according to the work of Taarning et al.[2] In a typical experiment, 1.25 mmol of DHA, 4 g methanol and 80 mg Sn-Beta were added to a 3 mL thick-walled glass reactor. The reactor was placed in temperature-controlled aluminum heating block set to 70° C. with 500 rpm stirring. After reaction for various times, the glass reactors were quenched in ice for 15 min, dried, and weighed before opening to make sure no leaking during the reaction.

Sample Analyses

For the reactions with pentose and hexose, sample analyses were performed using liquid chromatography (Shimadzu LC-20AT). Sugars were detected with a RI detector (RID-10A), and other products were detected with a UV-Vis detector (SPD-20AV) at wavelengths of 210 and 254 nm. The HPLC column used was a BIO-RAD HPX-87H sugar column. The mobile phase was 0.005 M $H_2SO_4$ flowing at a rate of 0.6 mL/min. The column oven was set to 30° C. DHA and ML were detected on an Agilent 6890 gas chromatography equipped with an FID-detector and a Restek RTX-VMS capillary column (30.0 m/0.25 mm id/1.4 pun film thickness). A helium flow rate of 6.0 mL/min pressurized at 1.498 bar was used. The oven temperature program is as follows: the initial temperature is 50° C. (hold 2 min) and then heated to 240° C. (ramp 20° C./min, hold 20 min).

What is claimed is:

1. A method of synthesizing molecular sieves, said method comprising the steps of:
    a) preparing a seed solution comprising aluminosilicate zeolite beta nanocrystals,
    b1) dealuminating said nanocrystals,
    b2) preparing a suspension of the dealuminated nanocrystals without drying,
    c) preparing a solution comprising a structure directing agent and a heteroatom source,
    d) adding the suspension of dealuminated nanocrystals to the solution of step c),
    e) allowing a gel to form,
    f) heating said gel at a temperature and a time sufficient to form a solid,
    g) filtering, washing and drying said solid, and
    h) calcining said solid.

2. The method of claim 1, wherein said gel is heated to at least 175° C. for 12 hours or less.

3. The method of claim 1, wherein said gel is heated to 200° C. for 6 hours.

4. The method of claim 1, wherein said aluminosilicate zeolite beta nanocrystals are well-crystalline 200 nm crystals comprising a crystallinity equal to or greater than 80% crystalline.

5. The method of claim 1, wherein said seed solution is a stable suspension comprising well dispersed beta zeolite seeds.

6. The method of claim 1, wherein said dealuminating step comprises directly treating said seed solution with a concentrated nitric acid solution.

7. The method of claim 1, further comprising collecting, washing and dispersing said dealuminated nanocrystals in liquid prior to step d).

8. The method of claim 1, wherein said structure directing agent comprises a compound selected from the group consisting of tetraethylammonium hydroxide solution (TEAOH), tetrabutylammonium hydroxide, tetramethylammonium hydroxide, 4,4'trimethylene bis(N-methyl N-benzyl-piperidinium) hydroxide, 1,2-diazabicyclo 2,2,2 octane, and dialkylbenzyl ammonium hydroxide.

9. The method of claim 1, wherein said heteroatom source comprises a compound selected from the group consisting of tin butoxide, $SnCl_4$, $SnCl_2$, $SnO_2$, tin(II)acetate, tin ethoxide, tin propoxide, metallic tin, amorphous silica, tetraalkylorthosilicate, colloidal silica, fumed silica, silica gels, titanium tetrachloride, titanium ethoxide, titanium isopropoxide, titanium butoxide, zirconium oxychloride, zirconium propoxide, zirconium butoxide, zirconium ethoxide, iron chloride and iron nitrate.

10. The method of claim 1, wherein said solution of step c) further comprises tetraethylorthosilicate (TEOS) and hydrofluoric acid (HF).

11. The method of claim 1, wherein said formed gel has a composition comprising $SiO_2$:0.5TEAOH:0.5HF:7$H_2O$.

12. The method of claim 1, wherein said formed gel has a composition comprising $SiO_2$:0.54TEAOH:0.54HF: 0.008$SnO_2$:7.5$H_2O$.

13. The method of claim 1, wherein said solid obtained in step h) is a zeolite selected from the group consisting of Sn-Beta, Si-Beta, Ti-Beta, Zr-Beta and Fe-Beta.

14. The method of claim 1, wherein said solution of step c) further comprises tetraethylorthosilicate (TEOS) and ammonium fluoride ($NH_4F$).

15. The method of claim 1, wherein said formed gel has a composition comprising $SiO_2$:0.54TEAOH:0.54$NH_4F$: 0.008$SnO_2$:7.5$H_2O$.

16. The method of claim 1, wherein said solution of step c) further comprises a caustic medium having a pH in the range of about 9 to about 13.

17. The method of claim 16, wherein said caustic medium is selected from the group consisting of sodium hydroxide (NaOH) and potassium hydroxide (KOH).

18. The method of claim 1, wherein said formed gel has a composition comprising $SiO_2$:0.008$SnO_2$:0.22$TEA_2O$:0.034 $Na_2O$.

* * * * *